(12) United States Patent
Gunther

(10) Patent No.: US 6,858,178 B2
(45) Date of Patent: Feb. 22, 2005

(54) COMPOSITION OF POROUS ELEMENT FOR BIOMATERIAL

(75) Inventor: Victor E. Gunther, Tomsk (RU)

(73) Assignee: Bio-Smart, Ltd., Ulsan (KR)

( * ) Notice: Subject to any disclaimer, the term of this patent is extended or adjusted under 35 U.S.C. 154(b) by 0 days.

(21) Appl. No.: 10/471,168

(22) PCT Filed: Feb. 20, 2002

(86) PCT No.: PCT/KR02/00267

§ 371 (c)(1),
(2), (4) Date: Sep. 4, 2003

(87) PCT Pub. No.: WO02/070028

PCT Pub. Date: Sep. 12, 2002

(65) Prior Publication Data

US 2004/0078086 A1 Apr. 22, 2004

(30) Foreign Application Priority Data

Mar. 5, 2001 (RU) .......................................... 2001106244

(51) Int. Cl.⁷ .............................................. C22C 19/05
(52) U.S. Cl. ........................ 420/452; 75/415; 148/428; 264/628; 419/2; 428/613
(58) Field of Search ................................ 420/450, 452; 148/428; 419/2; 75/415; 264/628; 428/613

(56) References Cited

U.S. PATENT DOCUMENTS

| 4,750,944 A | * | 6/1988 | Snyder et al. | ............... 148/522 |
| 4,877,435 A | * | 10/1989 | Haeberle et al. | ............... 65/515 |
| 5,071,437 A | | 12/1991 | Steffee | |
| 6,632,299 B1 | * | 10/2003 | Harris | ........................ 148/428 |

FOREIGN PATENT DOCUMENTS

| WO | WO 94/16646 | 8/1994 |
| WO | WO 98/19617 | 5/1998 |

* cited by examiner

*Primary Examiner*—John P Sheehan
(74) *Attorney, Agent, or Firm*—Jones Day

(57) ABSTRACT

A composition of a porous body for use as biomaterial according to the present invention is produced by adding Al (aluminum) in the amount of 0.1 to 3.0 atomic % to a porous composition consisting of titanium, nickel, iron and molybdenum, and it promotes the growth of living tissue and cells into pores. By the addition of Al to Ni, Ti, Fe and Mo, the temperature of formation of the liquid phase is lowered, and thus the diffusion of the constitutional elements of the composition is promoted, and the uniform distribution of the constitutional elements increases. As a result, the proportion of micropores in the porous body becomes increased to the extent that the distribution of micropores having the size in the range of $10^{-2}$ μm~10 μm is more than 5% in the metal bridge.

1 Claim, 1 Drawing Sheet

COMPOSITION OF POROUS ELEMENT FOR BIOMATERIAL

FIELD OF THE INVENTION

The present invention relates to an alloy composition of TiNi porous body for utilizing as biomaterial, and more particularly to an alloy composition comprising a Ti—Ni—Fe—Mo alloy material and aluminum (Al), which causes an increased number of micropores in a porous body and thus causes the growth of cells and living tissue to be activated as biomaterial.

BACKGROUND OF THE INVENTION

Generally, a porous alloy primarily comprising Ti—Ni, with Fe and Mo added thereto, has been manufactured by the method of self-propagating high temperature synthesis (hereinafter referred to as "SHS") and has been extensively used as biomaterial in the medical field due to its pore structure, good mechanical properties, high biocompatibility, and functional properties such as shape memory effect and pseudoelasticity.

For example, in the field of surgery, in order to prevent the secondary infection on an open infected area and to provide an advantageous condition for regeneration of living tissues, the porous body was used by impregnating the pores therein with antibiotics, and satisfactory results have been obtained. Further, the porous TiNi based alloy has been used in the field of tissue engineering, wherein living cells are cultivated in vitro and transplanted to a living body to replace living tissue. Furthermore, in the field of orthopedics surgery, the porous TiNi based alloy has been used as a scaffold which plays a role of an incubator for cultivating living tissue and cells and is transplanted to a living body as an artificial bone or a bone replacement. It is the porous structure that allows the transport of body fluid and provides advantages for the in-growth of new bone tissue into the pore, making the fixation of implant more natural and reliable.

The characteristics of pores in the porous body such as porosity, mean pore size, and the distribution of pore sizes are very important in determining whether the porous body can be applied to various medical fields as biomaterial, since physical and mechanical properties of the porous body such as shape memory, pseudoelasticity, fatigue resistance, and mechanical stability depend on the characteristics of pores. If the porous TiNi based alloy having small pores or micropores of a size in the range of $10^{-2}$ μm~10 μm in a metal bridge is used as a scaffold, the adaptability of the porous body as biomaterial can be highly enhanced.

Controlling pore sizes and their distribution, which constitute the characteristics of pores of the porous body, depends on the composition ratios of the components of the porous alloy composition and the procedural variables of the self-propagating high temperature synthetic method.

In a composition of a conventional porous body for medical purposes, which comprises titanium, nickel, iron and molybdenum, problems were encountered in that the distribution of micropores of the porous body having the size in the range of $10^{-2}$ μm~10 μm is less than 5% in the metal bridge.

However, in order to provide an alloy composition used as an effective and useful biomaterial wherein the growth of tissue and cells into pores is increased and the characteristics of the porous body as biomaterial are improved, the distribution of micropores should be more than 5%.

DISCLOSURE OF THE INVENTION

An object of the present invention is to provide a composition of a porous body for use as biomaterial which substantially obviates the problems caused by limitations and disadvantages of the prior art. That is, according to the present invention, a composition of a porous body for use as biomaterial, which is produced by adding Al (aluminum) to a porous composition consisting of titanium, nickel, iron and molybdenum, and by which the distribution of micropores is increased, so that the growth of living tissue and cells into pores can be increased, is provided.

These and other advantages and purposes of the present invention are achieved by a composition of a porous body which consists of nickel, titanium, iron and molybdenum and further comprises aluminum to promote the distribution of micropores.

By the addition of aluminum to the components of nickel, titanium, iron and molybdenum, composition ratios of the components are changed, and thus, the distribution of micropores becomes considerably increased.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

PREFERRED EMBODIMENTS OF THE INVENTION

Figure 2:
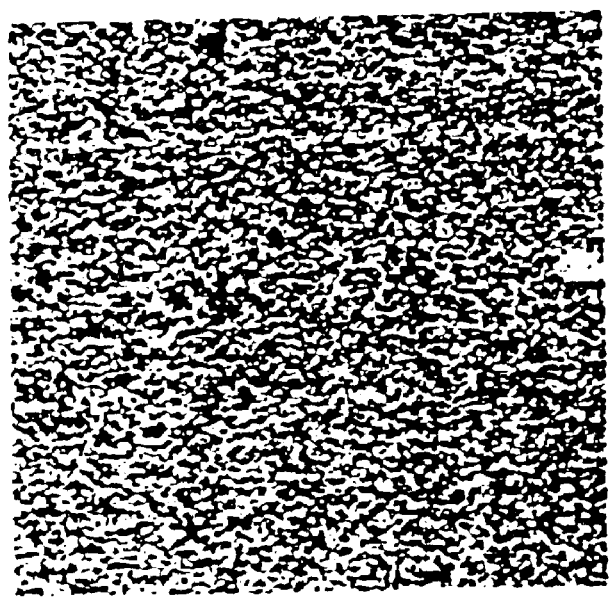
FIG. 2 is a microscopic photograph showing the structure of pores formed on the surface of the porous body composition for use as biomaterial, which comprises titanium, nickel, iron, molybdenum and aluminum according to a preferred embodiment of the present invention.

Reference will now be made in detail to preferred embodiments of the present invention, an example of which is illustrated in FIG. 2.

Composition ratios of a preferred embodiment are summarized in the following Table 1. It is apparent to those skilled in the art that the component ratios as shown in Table 1 are not to limit the present invention but simply illustrate a preferred embodiment of the present invention.

TABLE 1

Composition ratios of the composition according to a preferred embodiment

| Components | Ratio (atomic %) |
| --- | --- |
| Nickel (Ni) | 48.0~52.0 |
| Iron (Fe) | 0.02~3.0 |
| Molybdenum (Mo) | 0.1~2.0 |
| Aluminum (Al) | 0.1~3.0 |
| Titanium (Ti) | 40.0~51.78 |

The most characteristic feature of the present invention resides in the change of composition ratios caused by the addition of aluminum to titanium, nickel, iron and molybdenum. Preferred composition ratios are 48.0~52.0 atomic % of nickel, 0.02~3.0 atomic % of iron, 0.1~2.0 atomic % of molybdenum, 0.1~0.3 atomic % of aluminum and 40.0~51.78 atomic % of titanium, as listed in the above Table 1.

The reasons for the addition of aluminum and the results thereof are experimentally proved, and they can be explained by referring to the SHS process.

The SHS process is simple and highly advantageous in terms of energy. That is, in the SHS process, powders of components constituting a composition are mixed according to relevant composition ratios and formed in a certain shape, and then the shaped body is ignited at one end thereof. By the ignition of the shaped body in high temperatures, combustion occurs on the surface of the shaped body, and it propagates by itself through the surface of the body, to form a porous body.

In the SHS process, micropores in the porous body are formed during the course of rearrangement of the liquid phase formed by the combustion in high temperatures and the gases generated by the evaporation of impurities on the surface of the shaped body.

The combustion of the raw material powders occurs on the surface of the shaped body, and the propagation of the reaction is controlled by the diffusion of the components of the composition. By the addition of a component of the alloy, i.e., aluminum in the present invention, the melting point of the composition at which the liquid phase is formed changes, and such a change greatly influences on the area where the liquid phase exists and the rearrangement of the liquid phase.

Specifically, when Al is added to Ni, Ti, Fe and Mo, the melting point, i.e., the temperature of formation of the liquid phase is lowered, and thus the range of temperatures in which the liquid phase can be formed by combustion becomes wide.

In addition, as the range of temperatures where the liquid phase is formed is expanded, the diffusion of the constitutional elements of the composition in the liquid phase is promoted, and the uniform distribution of the constitutional elements increases, and as a result the proportion of micropores in the porous body becomes increased to the extent that the distribution of micropores having the size in the range of $10^{-2}$ μm~10 μm is more than 5% in the metal bridge.

Furthermore, the composition ratios of the constitutional elements are changed by the addition of Al to Ni, Ti, Fe and Mo, and thus the temperature of initial ignition in the SHS process becomes lower than the temperature required for the combustion of the composition consisting of Ni, Ti, Fe and Mo. This indirectly proves that the temperature range where the liquid phase is formed becomes expanded.

Preferably, the composition ratio of aluminum in the composition according to the present invention is 0.1 to 3.0 atomic %.

If the composition ratio of aluminum is less than 0.1 atomic %, the addition of Al does not increase the distribution ratio of micropores in the porous body, and even the distribution of micropores becomes decreased.

If the composition ratio of aluminum is more than 3.0 atomic %, the liquid phase is excessively formed, and micropores are not sufficiently formed, so that the porosity of the porous body deteriorates.

Therefore, it is not preferred that Al is added in the ratio of less than 0.1 atomic % or more than 3.0 atomic %.

Meanwhile, in the porous body composition according to the present invention, titanium and nickel are used since the mixed powders of titanium and nickel causes the composition to have pseudoelasticity which is substantially similar to the elasticity of bones of the human body. Also, they cause the composition of the present invention to have an excellent biocompatibility to the bone structure of the human body, so that the composition can be used as biomaterial such as in implants for teeth.

Further, the use of molybdenum (Mo) improves the stability of the phase in the synthetic process with titanium and nickel powders.

The composition of a porous body for use as biomaterial according to the present invention was prepared by the SHS process to form a certain proportion of micropores of the size in the range of $10^{-2}$ μm to 10 μm.

Specifically, Ni, Ti, Fe, Mo and Al powders were prepared according to the composition ratios as shown in Table 1, that is, Ni 48.0~52.0 atomic %, Fe 0.02~3.0 atomic %, Mo 0.1~2.0 atomic %, Al 0.1~3.0 atomic % and Ti 40.0~51.78 atomic % by measuring weights of the respective raw material powders. Each of the raw materials was weighed within the accuracy of ±0.1 mg, and the weight of the entire composition was within the accuracy of ±10 mg.

The raw material powders were mixed in a powder mixing machine under the environment of inert argon gas for 6 to 8 hours according to a dry mixing process.

The powder mixture was dried in a vacuum chamber under a temperature of 350 to 360K for about 7 hours. The holding of the powder mixture at this temperature for about 6–8 hours is sufficient for removal of the moisture and for reliable ignition and further combustion of the mixture. Then, the powder mixture was consolidated by tapping method.

The consolidated powder mixture was placed in a cylinder reactor made of stainless steel, and the reactor was ventilated with inert gas (Ar gas). Argon gas was supplied in a constant pressure, and the powder mixture was heated in a furnace by applying power to an ignitor.

Then, when the heating process was completed, the reactor was evacuated from the furnace and then it was cooled with water and during this procedure the inert Ar gas was continuously supplied.

Figure 1:
FIG. 1 is a microscopic photograph showing the structure of pores formed on the surface of a porous body composition for use as biomaterial, which consists of titanium and nickel.

The porous body manufactured by the above procedures had the porous structure in which micropores of $10^{-2}$ μm~10 μm are formed in the proportion of more than 5%. It is compared with the conventional porous body manufactured by the alloy of Ni, Ti, Fe and Mo only as shown in FIG. 1.

INDUSTRIAL APPLICABILITY

The alloy composition according to the present invention, which is characterized in that aluminum is added to the porous Ti—Ni—Fe—Mo alloy material, has an increased proportion of micropores of $10^{-2}$ μm to 10 μm more than 5% and thus activates the growth of cells and living tissue in the porous body. Therefore, the alloy composition according to the present invention can be used as biomaterial, and it can be applied to various medical fields.

It will be apparent to those skilled in the art that various modifications and variations can be made to the present invention without departing from the spirit and scope of the invention. The present invention covers the modifications and variations thereof provided they come within the scope of the appended claims and their equivalents.

What is claimed is:

1. A composition, of a porous body for use as biomaterial comprising Ni, Ti, Fe, Mo, and Al to increase the distribution of micropores in the porous body, wherein composition ratios of Ni, Ti, Fe, Mo and Al in the composition are respectively Ni 48.0 to 52.0 atomic %, Ti 40.0 to 51.78 atomic %, Fe 0.02 to 3.0 atomic %, Mo 0.1 to 2.0 atomic % and Al 0.1 to 3.0 atomic %.

* * * * *